US006775774B1

(12) United States Patent
Harper

(10) Patent No.: US 6,775,774 B1
(45) Date of Patent: Aug. 10, 2004

(54) OPTICAL CARD BASED SYSTEM FOR INDIVIDUALIZED TRACKING AND RECORD KEEPING

(75) Inventor: Jack Harper, Lakewood, CO (US)

(73) Assignee: BSI 2000, Inc., Lakewood, CO (US)

( * ) Notice: Subject to any disclaimer, the term of this patent is extended or adjusted under 35 U.S.C. 154(b) by 0 days.

(21) Appl. No.: 09/454,717

(22) Filed: Dec. 6, 1999

(51) Int. Cl.[7] .............................. H04K 1/00; H04L 9/00; G06F 17/60
(52) U.S. Cl. ....................... 713/186; 713/193; 713/194; 235/386; 705/14; 705/76
(58) Field of Search ................................ 713/186, 187, 713/193, 194; 235/386, 444, 455, 462, 487, 488, 490, 900, 382.5; 340/5.33, 5.83; 705/14, 16

(56) References Cited

U.S. PATENT DOCUMENTS

| 5,214,699 A | * | 5/1993 | Monroe et al. ............. 713/186 |
| 5,268,963 A | * | 12/1993 | Monroe et al. ............. 713/186 |
| 5,412,727 A | * | 5/1995 | Drexler et al. ............. 713/186 |
| 6,266,647 B1 | * | 7/2001 | Fernandez .................. 705/14 |
| 6,473,861 B1 | * | 10/2002 | Stokes ........................ 713/193 |

* cited by examiner

Primary Examiner—Emmanuel L. Moise
(74) Attorney, Agent, or Firm—Townsend and Townsend and Crew LLP

(57) ABSTRACT

A self contained system for identifying and storing information pertaining to an individual, the information including biometric information about the individual, the information being stored on an optical card. The system includes a read write system adapted for digitally reading from and writing to the digital card. A device for obtaining biometric data from an individual is also attached to the system. A data processing and storing system provided in communication with the read write device and the device for obtaining biometric data to compare data from the optical card and the data obtained from the device for obtaining biometric data, and then deliver data to the read write system for writing on the optical card. Additionally, a display for displaying data from the data processing and storing system is also included, so that the individual is identified by an image displayed on the display and by the comparison of biometric data obtained from the individual and biometric data stored in the card, and so that information pertaining to the comparison is encoded on the card by the read write system.

18 Claims, 7 Drawing Sheets

MedSAPh 2000

Bryan M. Luman
DOB 07/22/1965   Age 33 yrs
Male  Ht. 6'-3"   Wt. 200 lbs.
  Dr. Johnson
  Family Practice
  Yellow Choice HMO
  Plan: Yellow Plan
  Ply: 123456789  Grp:12432

Vitals / Medications
Temp. _98.9_   B.P. _110/71_
P. _19_   R. _49_

Medications:
Antibiotics, 3 pills, 3 times daily
Margrin, 2 pills, 2 times daily
Cutine, 1 pill (take as needed)

Complaints: _Patient has a potential head problem, patient steadily having arrhythmia & fatigue, no separate head attack._

History:
05/06/1999  PALCODEMF
05/05/1999  4 HOURS CO DEN PAIN 4 HOURS NAUSIA
01/03/1999  Visit 2
25/05/1998  Visit 1
25/05/1998  Sinus Headaches - Stress pol.

Treatments: _Immediate blood work, possible infection, hospital visit in 3 days._

Investigation: _Bryan seems to be helped with lots of extraordinary exercise and cardio therapy._

Physical:
  HEENT   MSK
  NECK          GIO
  CHEST   NEURO
  (HEART)  MENSTAT
  ABD           EXT

Follow up / Labs: _call for follow-up blood work in one week._

Signature: _Bryan Luman_

Codes: _N/A_

FIG. 3B

ACTIVE
11/11/1999 15:43
BSI2000 Test, 1234
BSI2000, Inc. - President
Jack Harper,123.45.6789
male age 47 5' 11" 190 lbs
Brown hair Green eyes

DRUG AND ALCOHOL TEST

Tested Clean
DOT 3.14
03/19/1997 First Test
03/25/1999 Last Test

TRAINING

01/30/1996 Welder
02/10/1996 Stainless Vessels
04/12/1998 GMT 2.14
05/13/1998 EMT 23.12
01/12/1998 GDR 2.1
03/11/1997 EDT 3.122
02/19/1997 HDS 4.1
05/30/1998 SKA 3.12
06/10/1997 EDP 9.1
05/30/1998 No Limitations

MEDICAL

05/30/1998 Pulmonary Function Test
                                  No Respirator
07/30/1998 Blood Heavy Metal Content Test
02/01/1999 Hearing Loss Test    30% Normal
12/25/1998 Physical Examination
                                  Good Health
Rehired & Signed by Garth

---

5F3CCA01F0A47FBE95CB790C395606F35365100

FIG. 4

OPTICAL CARD BASED SYSTEM FOR INDIVIDUALIZED TRACKING AND RECORD KEEPING

BACKGROUND OF THE INVENTION (a) Field of the Invention

This invention generally relates to a system for acquiring and storing information and storing this information in a single portable storage device. More specifically, but not by way of limitation, the system provides a display for displaying identification information carried on the storage device, a biometric identification device, a data processor, and a telecommunications port or communication device.

(b) Discussion of Known Art

There are many known devices or systems that allow the identification and tracking of information relating to an individual. A well known example of such systems includes the use of an identification card that includes a photograph and a magnetic machine readable stripe. These systems have gained considerable popularity because of their low cost and ease of use. The limitations of these systems, however, has left important un-met needs in terms of security, reliability and versatility.

More specifically, cards that include an individual's picture or facsimile, suffer from the limitation that the picture can be altered with relative ease. Additionally, the wide use of these systems, which rely on somewhat antiquated printing and reproduction techniques, has made the complete falsification or creation of false identity cards possible for individuals with modest technical training. Thus the problem of identity falsification by way of these systems persists.

Still further, the use of magnetic strips or magnetically encodeable portions in identification systems, relies on cards that are susceptible to inadvertent erasure of the cards by exposure to a strong magnetic field, as may be found on a cashier's counter, a speaker, or other commonly used tools or devices. Thus the reliability or effectiveness of these systems is susceptible to destruction or alteration with common tools or devices.

Still further, magnetically encoded identification cards as suffer from the limitation that they can only hold a limited amount of information. Thus, magnetically encoded cards may include identification codes which may be used as a key for comparison with an access code that is manually entered or provided by the user. Thus, these devices can offer only limited identification verification since the amount of information that can be stored as a key is also very limited. This limitation often allows thieves to simply spy on the user as he or she enters the key or verification information to gain access to all of the information needed to duplicate the access card.

Therefore, a review of known devices reveals that there remains a need for a versatile system that can be used to carry identification and identification verification information.

Still further, there remains a need for a system that allows storage of large amounts of information in a reliable, preferably encrypted manner, such that the criteria for verification can be increased in detail as well in manner. Thus, there remains a need for a system that provides for a method for identification verification by biometric factors, such as fingerprints, pupil patterns, and so on.

There remains a need for a versatile, reliable, and secure system for identification which also allows the progressive addition and storage of information to allow use of the stored information in the implementation of programs such as drug testing or substance abuse monitoring programs, employee tracking programs, or individualized record keeping and medical history tracking.

SUMMARY

It has been discovered that the problems left unanswered by known art can be solved by providing an optical card based system that includes:

- a device for reading from and writing on optical cards;
- a memory and processor for manipulating information obtained from the optical card;
- a display for displaying information obtained from the card; and
- a biometric data gathering device for obtaining biometric information from the person presenting the card.

According to a highly preferred embodiment of the invention the biometric information or data gathering device includes a fingerprint reading device which collects the image of at least one fingerprint from a hand of the person presenting the optical card. It is preferred that the optical card contain encrypted information about the fingerprint of the owner or duly authorized user of the card. The fingerprint image information is then used to compare the image with the stored image. The stored image being the image of the authorized user as recorded in the memory of the system. The comparison is carried out by the processor, which executes programs for the operation of the system. A similar comparison process would be carried out in the event that another biometric factor, such as the coloration or pattern on the individual's iris, for example.

Thus, the disclosed system will use encrypted computer code or writing to store information on the optical card, the information pertaining to biometric data, an image of the individual and information on the fact that the card had been used to access the system.

Because of the system's data processing and communications capabilities, it is contemplated that the system can be advantageously used for carrying out important identity verification and information storage and transfer processes. One such process or method is a method for employee or personnel tracking. Of particular importance is a system and method for implementing substance abuse or drug use programs at a facility. With this system and method it is contemplated that the optical card of the disclosed system would be used to store, in an encrypted manner, information pertaining to the identity of the card holder as well as certain risk characteristics about the individual and the area that is to be accessed.

The risk characteristics will be factors about the individual which will allow the system to determine a proper statistically derived frequency or model of random testing. For example, if the individual is of a high risk characteristic, either because of the job to be performed by that individual or because of the individual's personal history, then the system would select the proper statistical model to produce an adequate random determination for whether this individual should report to a drug testing facility for testing or continue through to work area.

Thus, to properly secure areas and administer the appropriate drug testing program, the optical card could also store information on the card holder's training, health, emergency assistance precautions or special needs in case of emergency may be stored on the optical card.

Still further, it is contemplated that the disclosed system be used in conjunction with other data input devices, such as a bar code scanner. It is further contemplated that when used with a scanner type input device, the system may be used for the input and tracking of medical records of the individual card holder or owner. In this embodiment, the optical card would be used to carry a combination of scanned image information, typed or manually entered information, and information by code scanning.

The information obtained by code scanning would preferably be standard or commonly used terms or codes such as CPT codes, treatments, and observations used during the examination of patients. The scanned image storage capabilities of the optical card can be used to store the examining physician's notes, which preferably will also have been entered onto the card by way of the code scanner. For example, when a card holder arrives at a physician's office, the physician would use the disclosed system to access the medical records as encoded on the optical card. These records would be accessed from the optical card and displayed by the system on a screen or printed out by exporting the information from the disclosed system to a printer. Once the physician examines the patient, he then writes down his observations and prescriptions in a customary, well known manner.

The physician's notes are then read by an assistant, or data entry operator. The data entry operator transcribes these notes by using standardized comments or inputs as presented as a part of a series of bar codes, each bar code representing a commonly used term or observation in that area of medicine. Additionally, the actual notes or comments hand written by the physician are then scanned and the image recorded on the optical card along with the transcribed notes. This combination of transcribed notes and images will ensure accurate retrieval of the records, and provide the physician with a means for authenticating and certifying that the records were his notes.

The use of the optical card and system disclosed herein allows the owner of the card, or card carrier, to carry a single card with a large amount of information pertaining to that individual's identity and medical history so as to allow anyone with the disclosed system to access the information and decide on the appropriate course of treatment.

It will be appreciated that the disclosed system is a particularly versatile tool in that it can be used for a variety of tasks that require identification of an individual, coupled with the need to carry out data processing operations which pertain specifically to the individual identified by the card.

Still further, it will be appreciated that the disclosed invention provides a versatile system and method for implementing employee monitoring programs, and particularly programs designed for testing employees for substance abuse.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which:

FIG. 2 is a schematic showing the division of a single drawing into FIGS. 2A and 2B.

FIGS. 3A and 3B illustrate the input material for use with an embodiment of the invention.

FIG. 4 is an example of a printout of information or instructions provided by the system.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
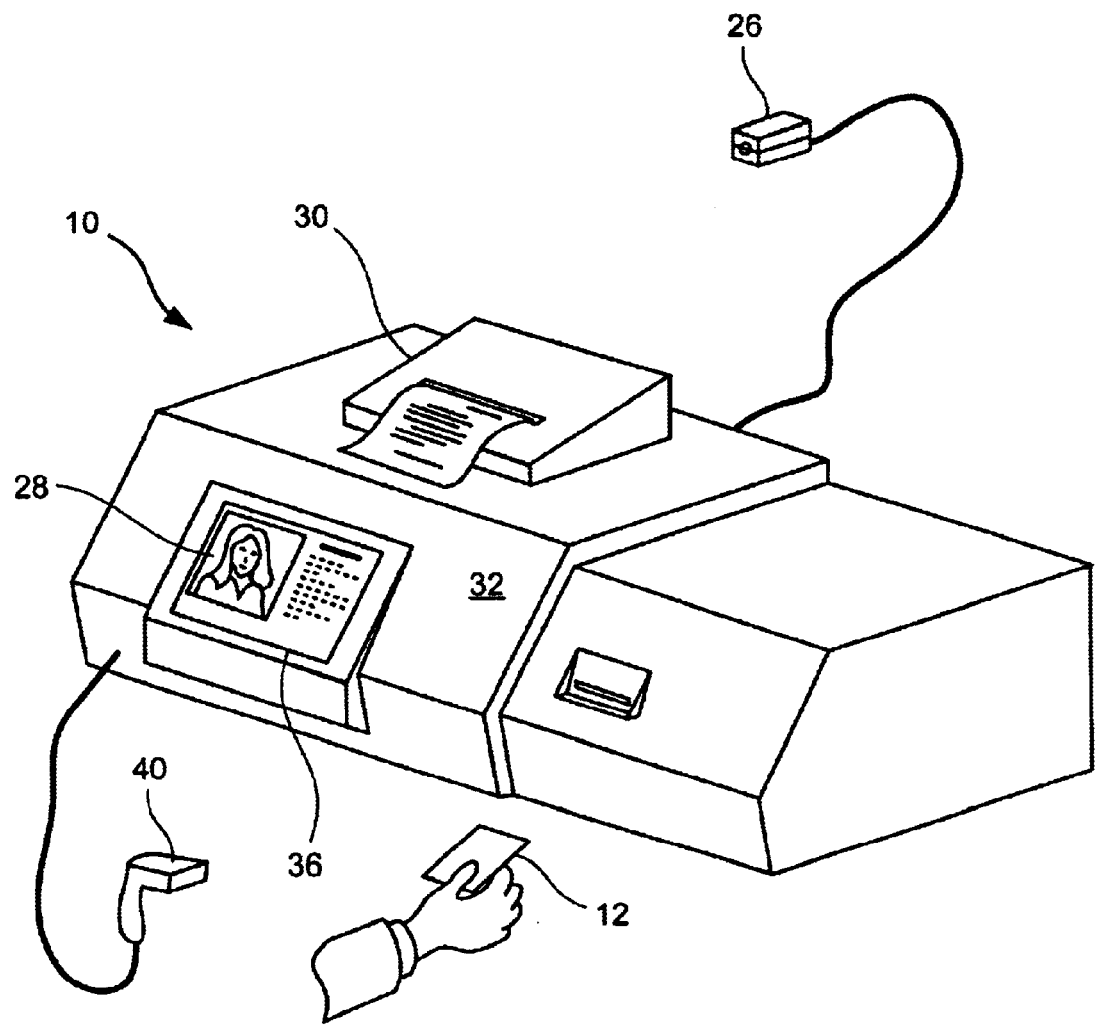
FIG. 1 is a perspective view of an embodiment of the invention, the view also illustrating the use with the addition of a barcode scanner.

Turning now to FIG. 1 where a self contained system 10, made in accordance with the principles taught herein, has been illustrated. The system 10 is particularly useful for identifying and storing information pertaining to an individual. According to a highly preferred embodiment of the invention, the system 10 uses an optical card 12 for storing the information pertaining to the individual. It is contemplated that this information pertaining to the individual may include information about the individual's health or physical characteristics, information about the fact that the system 10 and the optical card 12 were used together. And other data which is useful in carrying out calculations, such as statistical calculations pertaining to the individual, within the system 10.

Preferably, the optical card 12 will be of a well known write once, read many (WORM) type of the category or class of devices discussed in U.S. Pat. No 5,579,772. State of the art optical cards are capable of storing up to four megabytes of digital information. This translates into approximately 1500 type written pages. Thus, it is contemplated that state of the art optical cards are particularly well suited for use with the disclosed system 10. However, it is important to note that the principles taught herein are applicable to other highly transportable WORM type devices.

The system 10 will serve as a portable, self contained unit, that does not depend on a connection or data link to a larger data holding and processing unit. Thus, the user can simply place one of the systems 10 at a desired location in an office building, manufacturing plant, laboratory, and so on, and carry out all of the necessary identity verification and program implementation without having to establish communications with a central data processing center. The system 10 uses the data storage capabilities of the optical card 12 to store information such as photographs in a digital format, program parameters such as number of times that the optical card has been presented to the system 10, information about the card holder who is being tracked or identified by the system 10, this information may include medical history, substance abuse history, and job access requirements or authority to enter secured areas.

Figure 2A:
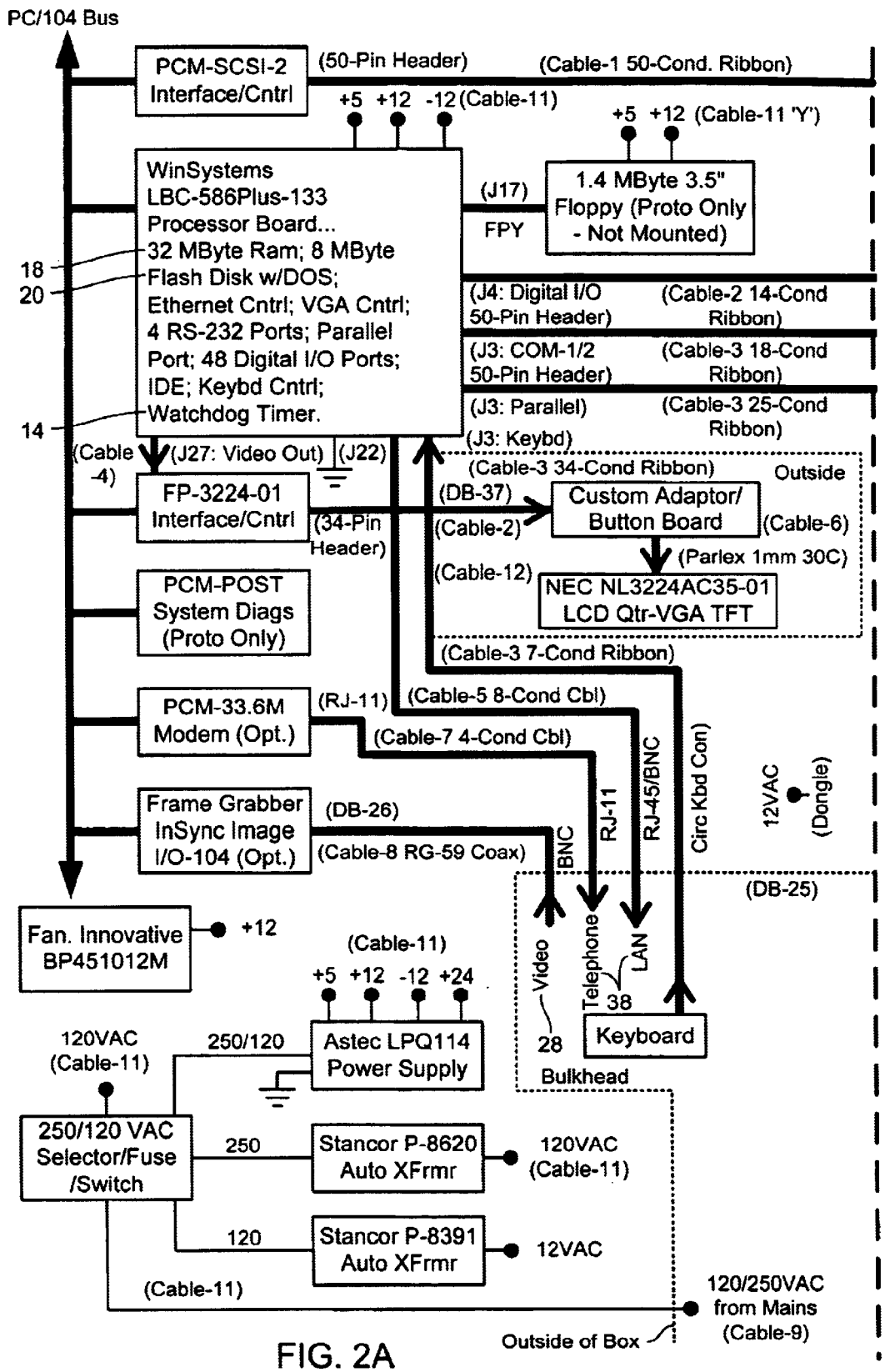
FIG. 2A and FIG. 2B are a schematic of the architecture of an embodiment of the invention.
Figure 2B:
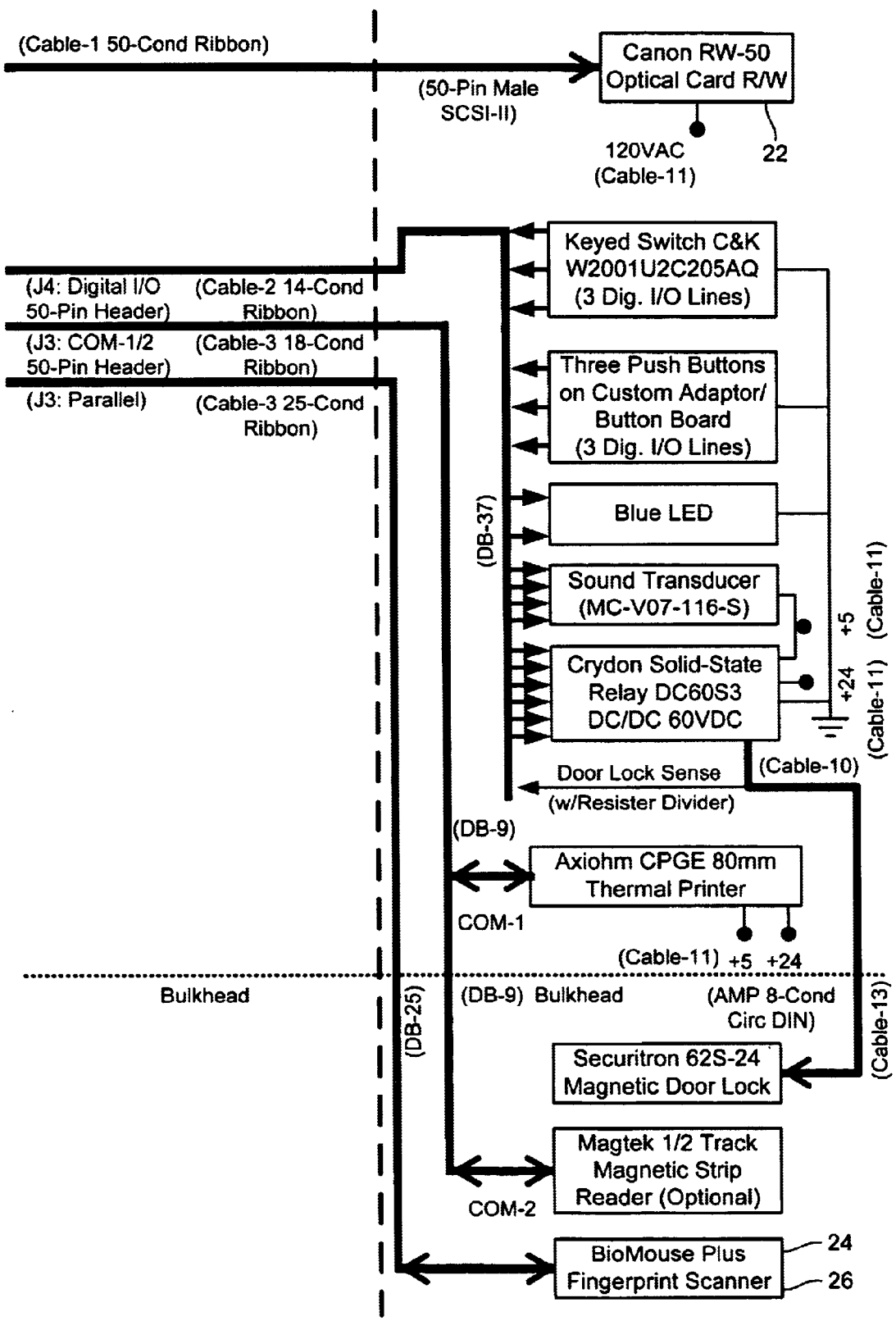

Thus, as shown on FIG. 2, it is contemplated that the system 10 will include data processing and storing means 14, which in a preferred embodiment will include a processor 16, such as an Intel 80X86 series type of processor. Additionally, it is contemplated that the system will include random access memory (RAM) 18, and a basic input and output system processing and access disk 20, such as a flash type disk which includes the system's disk operating system (such as Windows NT brand system).

Also shown on FIG. 2 is a read write means 22, which serves for reading data from the optical card 12 and writing data on to the optical card 12. In a highly preferred embodiment of the invention this read write means 22 is an optical card read/write apparatus manufactured and sold by the Drexler Technology Corporation of Mountain View, Calif. The read write means 22 is in communication with the data processing and storing means 14. The term "communication" as used herein means that data can be transferred from one device to the other. This data transfer may be carried out through optical fiber, electrical pulses, or other ways for allowing data transfer between two devices.

Information that has been stored on the optical card 12, preferably by way of a strong encryption method, is retrieved into the data processing and storing means. This information will include a digitized photograph of the card holder and biometric identification information, information about the cardholder's history, such as substance abuse and testing, training and qualifications, important medical limitations and emergency treatment information, and executable program information. The executable program information is a program which is downloaded from the card onto the data processing and storing means 14 where it is executed. In one highly preferred example of the invention this executable program is a drug testing program which suits the needs of a particular entity which is using the system 10. The drug testing program is executed by the data processing and storing means 14, which also used information retrieval from the optical card 12 as the data on which to carry out its operations.

Also shown on FIG. 2 is that a highly preferred embodiment of the invention will include means 24 for obtaining biometric data from an individual. According to a preferred example of the invention the means 24 for obtaining biometric data from an individual includes a fingerprint reading device 26 such as the fingerprint scanner sold under the trademark "BioMouse Plus" by the American Biometrics Company of Ottawa, Canada. It is important to note that while this preferred example uses a fingerprint scanner, it is also contemplated that other biometric scanning or reading devices may be employed with the system, such as iris pattern scanning devices or even DNA recognition devices as these become commercially viable.

The information generated by the means 24 for obtaining biometric data from an individual is then transferred to the data processing and storing means 14 where it is compared with a verified pattern from the card holder to positively identify that the true card holder is present before the system 10.

Once the verification of identity has been completed, the system 10 uses the executable program from the optical card 12 to implement the drug testing, record keeping, banking, or other programs, such as government assistance programs where funds are to be used by recipients for the purchase of specific items. The system 10 will then proceed to carry out the operations of the programmed task as controlled by the data encrypted on the optical card 12. The system then communicates with the cardholder by way of a video output 28, or display means, which displays the cardholder's picture and instructions about the access or transaction procedures. Additionally, it is contemplated that the system will include a printing means 30 which is used to provide the cardholder with a printed record of instructions or details about the interaction between the card user and the system 10.

It is important to note, that in a highly preferred embodiment of the invention the system 10 is self contained in that a display means 32, such as a liquid crystal display (LCD) or other display screen, the data processing and storing means 14, and the read write means 22, are all held by the same housing 32. It is contemplated that the means 24 for obtaining biometric data is connected to the system 10 by way of a cable or other communication device. However, it is contemplated that in furtherance of providing the benefits of a stand-alone system, the means 24 for obtaining biometric data may be attached or fixed to the housing.

The disclosed system offers important new and useful results in that it allows an entity to operate many systems 10 at various locations, without having to have the systems 10 networked together. The encryption and record keeping of transactions is all carried out by the each system 10 and recorded in an encrypted fashion on the optical card 12. Thus in going from location to location, the card holder will be received and handled as if the system 10 were part of a larger network connected computers.

It is also contemplated that the system 10 may include a keypad or other data input device, such as a voice activated input device, to allow the use of user entered instructions or passwords and the like with the system. It is also contemplated that the system may include a relay 34 for controlling access through a doorway or gate. Additionally, it is also important to note that it is contemplated that the system 10 could be connected to a telecommunications system or other data transfer system for transferring data to a central system or to another device. Adding a connection to a central system would allow the provision of a data backup system option to the disclosed invention.

As an example of the system 10 in use in air transport industry, the system 10 is used to control access to an aircraft maintenance work area. In this example, access to the secured work area is locked by a magnetic door lock that is controlled by the system 10. A card holder mechanic who is about to enter the work area will approach the system 10 and insert his optical card 12 into the system 10 and at the same time place at least one of his fingers on the means 24 for obtaining biometric data from an individual. Thus, when the optical card 12 is inserted into the it read write means 22, the read write means 22 has downloaded to the data storing and processing means 14 the executable programs that necessary for allowing the system 10 to compare biometric data obtained from the mechanic by the means 24 for obtaining biometric data. At the same time, a picture of the individual is presented on the screen, or display 36. The image on the screen can serve a means for identifying the individual by an attendant at the gate. If the comparison of the biometric information results in a positive identification, then the system initiate other routines that originate from executable programs stored in the optical card 12 itself, or may have been stored within the data processing and storing means. In this example, a drug testing program would be initiated. This program would weigh the sensitivity of the individual's duties, his drug test history, and his medical history, and run a random number or selection generation program to indicate whether this individual should be tested for controlled substances. Of course, other parameters than those enumerated above may be used. However, the individual is selected for drug testing, the system 10 would communicate to the individual by way of the display 36 and or by printing out a summary, similar to that shown on FIG. 4, of the time and place where the individual is to present himself for drug testing. Information about the requirement that the test be carried out would immediately be written on encrypted form on the optical card 12 by the read write means 22, so that any further use of the optical card 12 would have to follow an acceptable notation in the records held by the optical card 12 to the effect that a satisfactory test was carried out after the requirement was made.

Referring once again to FIG. 2, as discussed above, it is contemplated that the system 10 may also include telecommunications port 38 that may be used to instantaneously warn or inform a supervisor or other responsible individual of the test requirement, and thus the responsible individual may immediately escort the employee to the drug test facility. This immediate escort would minimize the possibility of an attempt to alter the drug test by ingesting large amounts of water or other dilutants, for example. Additionally, it would minimize the opportunity of obtaining a phony sample from a known drug free individual.

Still another application of the system 10 includes the use of a barcode scanner 40 for entering information into the system 10. The barcode scanner 40 would be in communication with the data processing and storing means 14 to allow the information entered into the system by way of the barcode scanner 40.

Figure 3A:
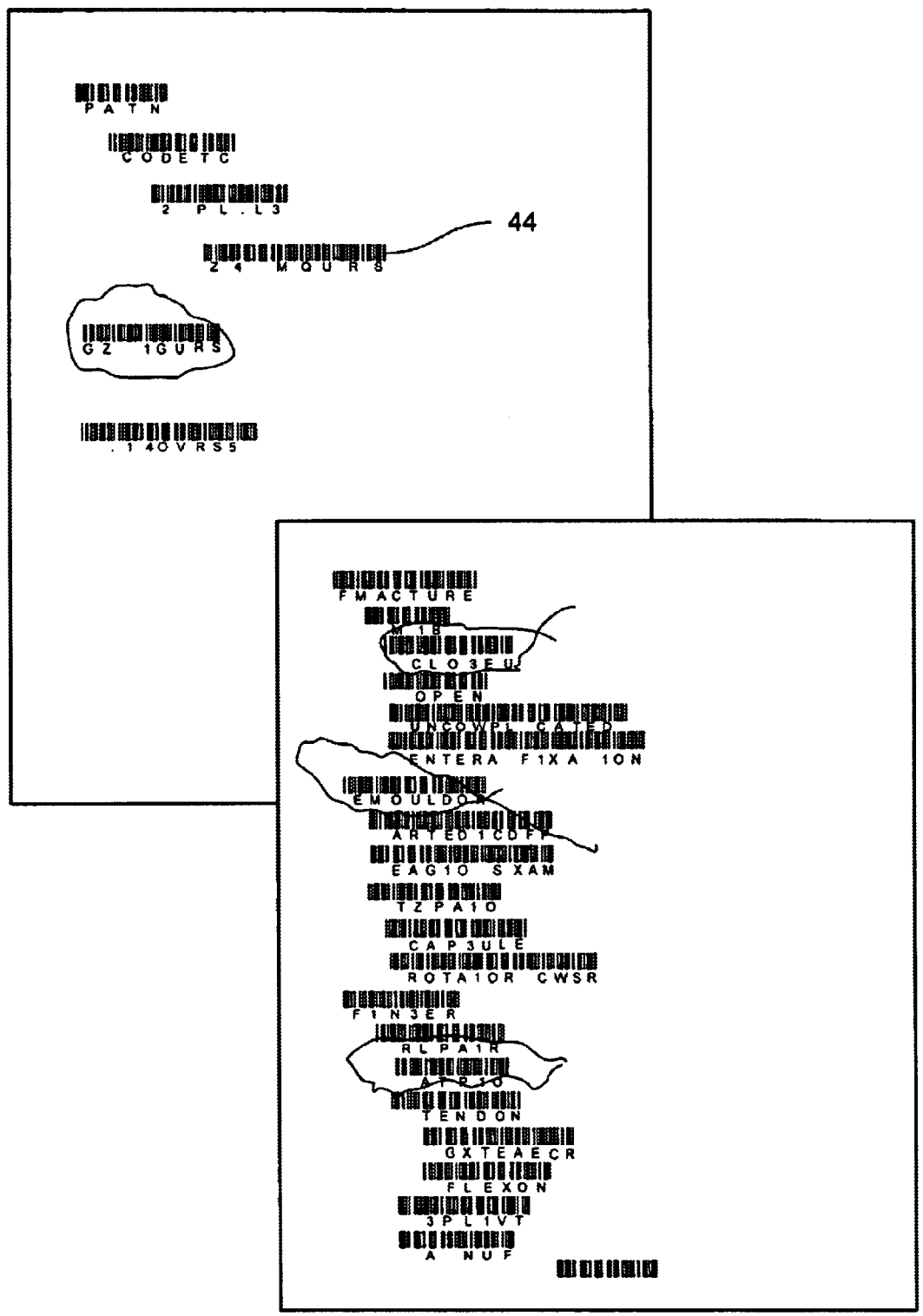

Referring now to FIGS. 1–3B, and particularly FIG. 3A and FIG. 3B, it will be understood that the addition of the barcode scanner 40 would allow the user to further harness the versatility of the disclosed system 10. In this embodiment, the system 10 is used for storage and retrieval of medical records. In use, a cardholder would arrive at a physician's office with his or her medical records stored as encrypted data stored in the optical card 12. The physician would then access the medical records by inserting the optical card 12 into the read write means 22, while simultaneously having the patient place a finger on the means 24 for obtaining biometric data from the patient. The system 10 would compare the biometric information, while the physician observes the display 36 to determine whether the patient presenting the card is in fact the person whose biometric characteristics are being verified for identification by the system 10. An additional benefit to including the image information on the optical card is that the physician may look at the image on the display 36 and compare that image with the patient's current appearance. Any changes in the appearance of the patient may aid the physician in the diagnosis of the patient.

Once the physician has retrieved the records stored on the optical card 12, and examined the patient, he may then write down recommendations and other observations. Of course, the physician may even take photographs of the patient for storage in a digital format in the optical card 12. These photographs may be used at a later time for further evaluation of the patient's progress. The physician's notes 42 are also stored in the optical card 12. However, these notes are stored in two forms. One form is in the form of an image, such as the photographs. These images serve a purpose in that they may be retrieved at a later date and aid the physician in refreshing his memory about the patient's visit. Since the diagnosis and observations about the patient's condition is likely to include many typical or commonly found observations. These comments or observations are at least in part found as terms associated with barcode 44 as shown on FIG. 3A and FIG. 3B. At the end of the patient's visit, the physician's notes 42 are encrypted into the patient's optical card. A physician's assistant then uses the barcode scanner 40 to transcribe the physicians's notes 42 into computer readable text that is also stored as encrypted data on the optical card. This text may include the prescription for the patient. The patient may then go to a pharmacy which provides the needed prescriptions and which posses a system 10. The optical card 12 and the system 10 are then used to verify the identity of the patient and to retrieve the prescriptions to be filled. The records of the transactions may then also be encripted on to the card. It is important to note that the encryption and data retrieval system and the programmability of the data processing and storing means 14 used to with the system 10 may be used to allow selective access to the records stored in the optical card 12. Thus the pharmacy would only be able to retrieve identification information and the prescriptions.

In still another variation of the use of the disclosed system, a method for tracking and controlling the inventory of work place tools or materials is disclosed. With this method, a tool crib or materials distribution center would maintain an inventory of tools or materials to be distributed to employees. These tools or materials would be inventoried by way of a barcode attached to the tool or material to be assigned to an employee.

When the employee needs to obtain a tool or material he will approach the tool crib or distribution center with his optical card 12. The tool crib or distribution center would possess a system 10, which would be used, as described above, to identify the individual cardholder. The system 10 would then access information stored in the card. This information would preferably include information about tools or materials that have been checked out by the card holder, employee. For example, if the employee is a nurse that is authorized to administer certain kinds of medication, this authority would be encripted on to the optical card 12. The system 10 would then use the information from the optical card to provide authorization to check out the equipment requested by the nurse or the medications requested by the nurse. Once authorized, the card holder would receive the materials from the tool or materials dispensing area. To inventory the release of these tools or materials, the person issuing the tools or materials would use the barcode scanner 40 to record the fact that these materials were issued to the card holder. Of course, it is contemplated that a double entry type system may be used, where a computer connected to the system 10 would deduct the materials form an inventory stored in its memory in addition to recording the transaction on the optical card 12. The disclosed system 10 would be used to record the event on the card holder's optical card 12. Additionally, the system 10 would also be used to record the return of tools or materials on the optical card 12.

By recording the fact that tools or other supplies have been assigned to the cardholder the system 10 can be used to control inventories of the tools by combining the use of the information recorded on the optical card 12 to control the ingress and egress to the work area. Thus the card holder would check out a tool from a tool crib within the secured area, the fact that the tool was checked out to the card holder would be recorded on the cardholder's optical card 12. The card holder would then use the tool to carry out his duties throughout the work day. At the end of the work day the card holder would be required to insert his optical card 12 into the system 10 that controls access to the work area. By inserting the card into the system 10, the system 10 would read from the card the fact that a tool was checked out by that card holder. If the tool has not been returned to the tool crib, the system 10 controlling access to the work area would not allow the person to leave until the tool was returned to the tool crib and the system 10 located at the tool crib used to record the return on the card 12.

Of course, it is contemplated that systems for allowing the override of the access control in case of fire or other a emergencies may be incorporated into the system without departing from the scope of the disclosed invention.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A self contained system for identifying and storing information pertaining to an individual, the information including biometric information about the individual, the information being stored on an optical card, the system comprising:
   read write means adapted for digitally reading from and writing in a digital format on the digital card;
   means for obtaining biometric data from an individual;
   data processing and storing means in communication with said read write means and said means for obtaining biometric data to compare data from said optical card and the data obtained from said means for obtaining biometric data and deliver data to the read write means for writing on the optical card; and
   display means for displaying data from said data processing and storing means, so that the individual is identified by an image displayed on the display means and by the comparison of biometric data obtained from the individual and biometric data stored in the card, and so that information pertaining to the comparison is encoded on the card by said read write means.

2. A system according to claim 1 wherein the data processing and storing means is programmed for encrypting and deciphering encrypted data obtained from said read write means.

3. A system according to claim 1 wherein said read write means, said means for obtaining biometric data from an individual, said data processing and storing means, and said display means are held in a single housing.

4. A system according to claim 1 and further comprising barcode scanning means in communication with said data processing means.

5. A system according to claim 1 and further comprising communication means for sending and receiving data to be processed with said data processing means.

6. A system according to claim 5 wherein said communications means is connected to an access control mechanism, so that on verification of the identity of person by way of the biometric data and comparison of the biometric data and selection by a predetermined analysis with the data processing means, access with the access control mechanism is controlled.

7. A self contained system for identifying and storing information pertaining to an individual, the information including biometric information about the individual, the information being stored on an optical card, the system comprising:
   means for obtaining biometric data from an individual;
   a housing containing:
      read write means adapted for digitally reading from and writing in a digital format on the digital card;
      data processing and storing means in communication with said read write means and said means for obtaining biometric data to compare data from said optical card and the data obtained from said means for obtaining biometric data and deliver data to the read write means for writing on the optical card; and
      display means for displaying data from said data processing and storing means, so that the individual is identified by an image displayed on the display means and by the comparison of biometric data obtained from the individual and biometric data stored in the card, and so that information pertaining to the comparison is encoded on the card by said read write means.

8. A system according to claim 7 and further comprising communication means for sending and receiving data to be processed with said data processing means.

9. A system according to claim 7 wherein said data processing and storing means is programmed for providing randomly assigning at a reading of the optical card the testing of the individual identified by information on the card for a controlled substance test.

10. A system according to claim 7 and further comprising a barcode scanning means in communication with said data processing means.

11. A system according to claim 7 and further comprising printing means within said housing, the printing means being in communication with said data processing means.

12. A system according to claim 7 wherein said means for obtaining biometric data from an individual comprises a fingerprint reading means.

13. A system according to claim 7 wherein said means for it obtaining biometric data from an individual comprises an eye pattern recognition means for recognizing patterns on a person's eye.

14. A method for tracking an individual and information about the individual, the method comprising:
   providing an optical card;
   assigning the optical card to the individual;
   providing a self contained system for identifying and storing information pertaining to the individual, the information including biometric information about the individual, the information being stored on the optical card, the system comprising:
      read write means adapted for digitally reading from and writing in a digital format to the digital card;
      means for obtaining biometric data from the individual;
      data processing and storing means in communication with said read write means and said means for obtaining biometric data to compare data from the optical card and the data obtained from said means for obtaining biometric data and deliver data to the read write means for writing on the optical card; and
      display means for displaying data from said data processing and storing means;
   obtaining biometric data from the individual being tracked with the means for obtaining biometric data;
   identifying the individual being tracked by producing an image displayed on the display means and by using the processing means for comparing the biometric the comparing biometric data obtained from the individual and biometric data stored in the card; and writing to the optical card with the read write means information about the identification, so that the information about the identification is stored in the optical card for future tracking.

15. A method according to claim 14 and further comprising associating controlled substance testing information with the identification, and assigning required testing for controlled substance use by the individual based on the identification, and writing the controlled substance testing information on the optical card with the read write means.

16. A method according to claim 14 and further comprising encrypting the information written on the optical card with the read write means.

17. A method according to claim 16 and further comprising providing digitized images of documents and associating said information on the identification with the digitized images of documents, and writing the associated information on the identification with the digitized images of documents to the optical card.

18. A method according to claim 16 and further comprising providing statistical data on required testing for controlled substances and associating said information on the identification with the information on required testing for controlled substances, and writing the associated information on the identification with the information on required testing for controlled substances to the optical card.

* * * * *